United States Patent
Mihota et al.

(10) Patent No.: US 12,099,020 B2
(45) Date of Patent: Sep. 24, 2024

(54) DETECTION DEVICE AND DETECTION METHOD

(71) Applicant: SONY GROUP CORPORATION, Tokyo (JP)

(72) Inventors: Norihito Mihota, Tokyo (JP); Sachio Iida, Tokyo (JP)

(73) Assignee: Sony Group Corporation, Tokyo (JP)

(*) Notice: Subject to any disclaimer, the term of this patent is extended or adjusted under 35 U.S.C. 154(b) by 177 days.

(21) Appl. No.: 17/995,574

(22) PCT Filed: Mar. 17, 2021

(86) PCT No.: PCT/JP2021/010948
§ 371 (c)(1),
(2) Date: Oct. 5, 2022

(87) PCT Pub. No.: WO2021/215151
PCT Pub. Date: Oct. 28, 2021

(65) Prior Publication Data
US 2023/0194440 A1    Jun. 22, 2023

(30) Foreign Application Priority Data
Apr. 20, 2020   (JP) ............................. 2020-074863

(51) Int. Cl.
*G01N 22/04*   (2006.01)
*G01S 7/4915*   (2020.01)

(52) U.S. Cl.
CPC ............ *G01N 22/04* (2013.01); *G01S 7/4915* (2013.01)

(58) Field of Classification Search
CPC ...... G01S 7/4915; G01S 13/885; G01S 7/024; G01R 27/2623; G01R 27/2676;
(Continued)

(56) References Cited

U.S. PATENT DOCUMENTS 4,817,021 A * 3/1989 Sowerby ............. G01N 33/222
                                                    250/359.1
5,315,258 A    5/1994 Jakkula
(Continued)

FOREIGN PATENT DOCUMENTS

CN    107966476    4/2018
CN    109342515    2/2019
(Continued)

OTHER PUBLICATIONS

"Applicability of Electromagnetic Wave to Determination of Chloride Ion Concentration in Concrete," Proceedings of the Japan Concrete Institute, vol. 26, Sep. 30, 2004, pp. 119-120. [no translation available; see figures].
(Continued)

*Primary Examiner* — Vinh P Nguyen
(74) *Attorney, Agent, or Firm* — Sheridan Ross PC

(57) ABSTRACT

An inspection device and method suppressing measurement time and power consumption. A detection device according to the present disclosure includes a first probe with a first antenna unit for transmission, a second probe with a second antenna unit for reception, the second probe being opposed to the first probe at a predetermined distance, a measurement unit that measures a measurement signal including a propagation characteristic of an electromagnetic wave in a medium between the first and second antenna units, and a calculation unit that calculates characteristics information of the medium based on the measurement signal. In a first mode, the measurement unit measures the measurement signal in a first frequency band for the electromagnetic wave propagating in the medium, and in a second mode, the measurement unit measures the measurement signal in a second frequency band, which is a part of the first frequency band for the electromagnetic wave.

22 Claims, 13 Drawing Sheets

(58) Field of Classification Search
CPC ............ G01R 29/0878; G01R 27/2617; G01R 31/11; G01R 31/088; G01R 31/2839; G06F 11/3058; G01N 29/036; G01N 29/022; G01N 29/46; G01N 27/221; G01N 33/246; G01N 22/02; G01N 27/223; G01N 2021/855; G01N 29/07; G01N 23/00; G01N 27/048; G01N 29/02; G01N 27/22; G01N 29/024; G01N 5/025; G01N 9/002; G01N 19/10; G01N 21/31; G01N 2223/052; G01N 2223/101; G01N 2223/613; G01N 22/00; G01N 29/24; G01N 29/2437; G01N 33/28
See application file for complete search history.

(56) References Cited

U.S. PATENT DOCUMENTS

| | | | | |
|---|---|---|---|---|
| 6,215,317 B1 * | 4/2001 | Siddiqui | ............... | G01N 33/246 |
| | | | | 324/637 |
| 6,963,205 B2 * | 11/2005 | Lundstrom | .......... | G01N 33/246 |
| | | | | 324/663 |
| 11,428,714 B2 * | 8/2022 | Yamada | ................. | G01R 29/08 |
| 2008/0234958 A1 | 9/2008 | Kupfer | | |
| 2020/0182906 A1 | 6/2020 | Yamada et al. | | |

FOREIGN PATENT DOCUMENTS

| | | |
|---|---|---|
| CN | 110678741 | 1/2020 |
| JP | H06-324162 | 11/1994 |
| JP | 2000-146867 | 5/2000 |
| JP | 2003-329613 | 11/2003 |
| JP | 2011-191208 | 9/2011 |
| JP | 2014-200030 | 10/2014 |
| JP | 2017-143459 | 8/2017 |
| JP | 2018-207403 | 12/2018 |
| WO | WO 2018/221051 | 12/2018 |

OTHER PUBLICATIONS

International Search Report and Written Opinion prepared by the Japan Patent Office on May 25, 2021, for International Application No. PCT/JP2021/010948, 3 pgs.

* cited by examiner

DETECTION DEVICE AND DETECTION METHOD

CROSS REFERENCE TO RELATED APPLICATIONS

This application is a national stage application under 35 U.S.C. 371 and claims the benefit of PCT Application No. PCT/JP2021/010948, having an international filing date of 17 Mar. 2021, which designated the United States, which PCT application claimed the benefit of Japanese Patent Application No. 2020-074863, filed 20 Apr. 2020, the entire disclosures of each of which are incorporated herein by reference.

TECHNICAL FIELD

The present disclosure relates to a detection device and a detection method.

BACKGROUND ART

A moisture sensor that measures the water content in a medium may employ a frequency domain refractometry (FDR) method. The FDR method is a method in which an electromagnetic wave is transmitted along a metal probe buried in a medium, and the water content in the medium is calculated from the relative permittivity measured on the basis of the reflection response of the electromagnetic wave.

CITATION LIST

Patent Document

Patent Document 1: WO 2018/221051 A

SUMMARY OF THE INVENTION

Problems to be Solved by the Invention

However, the moisture sensor employing the FDR method sweeps over a wide frequency band in order to measure the water content accurately. For this reason, the conventional moisture sensor requires long measurement time and high power consumption. In a device driven by a battery, such as a mobile terminal and an internet of things (IoT) device, the measurement time and the power consumption are directly linked to the battery duration. Therefore, reduction in measurement time and power consumption is desired.

In view of the above circumstances, an object of the present technology is to provide an inspection device and an inspection method capable of suppressing measurement time and power consumption.

Solutions to Problems

An inspection device according to an aspect of the present disclosure includes a first probe that includes a first antenna unit for transmission, a second probe that includes a second antenna unit for reception, the second probe being opposed to the first probe at a predetermined distance, a measurement unit that measures a measurement signal including information regarding a propagation characteristic of an electromagnetic wave in a medium between the first and second antenna units, and a calculation unit that calculates characteristics information of the medium on the basis of a characteristic amount obtained from the measurement signal. In a first mode, the measurement unit measures the measurement signal in a first frequency band for the electromagnetic wave propagating in the medium, and the calculation unit calculates the characteristics information of the medium on the basis of a first characteristic amount obtained from the measurement signal in the first frequency band, and in a second mode, the measurement unit measures the measurement signal in a second frequency band, which is a part of the first frequency band for the electromagnetic wave, and the calculation unit calculates the characteristics information of the medium on the basis of a second characteristic amount obtained from the measurement signal in the second frequency band.

In the first mode, the calculation unit may generate relationship information between the first characteristic amount and a partial characteristic amount on the basis of the partial characteristic amount obtained from the measurement signal in the second frequency band out of the measurement signal in the first frequency band, and in the second mode, the calculation unit may calculate the characteristics information of the medium by applying the second characteristic amount to the relationship information.

The second frequency band may be a band including a peak frequency at which an intensity of the measurement signal in the first frequency band is maximum.

In the first mode, the measurement unit may measure the electromagnetic wave at a first frequency spacing, and in the second mode, the measurement unit may measure the electromagnetic wave at a second frequency spacing wider than the first frequency spacing.

A width of the second frequency band may be substantially equal to a width of the first frequency band.

The second frequency band may be a specific frequency in the first frequency band.

The characteristic amount may be a propagation delay time of the electromagnetic wave between the first and second antenna units, a shape of a frequency characteristic of the electromagnetic wave, or a waveform of the propagation delay time obtained on the basis of the frequency characteristic of the electromagnetic wave.

The characteristic amount may be a phase or an amplitude of the electromagnetic wave at the specific frequency.

The calculation unit may include a delay time calculation unit that calculates a propagation delay time of the electromagnetic wave between the first and second probes as the characteristic amount on the basis of the measurement signal, a relative permittivity calculation unit that calculates a relative permittivity of the medium as the characteristics information on the basis of the propagation delay time, a water content calculation unit that calculates a water content in the medium on the basis of the relative permittivity, and a relationship information generation unit that generates the relationship information.

In the first mode, the calculation unit may calculate a first propagation delay time on the basis of the measurement signal in the first frequency band, calculate a partial delay time obtained from the measurement signal in the second frequency band out of the measurement signal in the first frequency band, and generate the relationship information using the first propagation delay time and the partial delay time, and in the second mode, the calculation unit may calculate a second propagation delay time on the basis of the measurement signal in the second frequency band, generate a corrected delay time obtained by converting the second propagation delay time into a propagation delay time in the first frequency band by applying the second propagation delay time to the relationship information, and calculate a relative permittivity of the medium and a water content in the medium using the corrected delay time.

A mode switching unit that switches between the first mode and the second mode may further be included.

In the second frequency band, an upper limit of a level of the transmission signal out of the first frequency band may be higher than an upper limit of a level of the measurement signal in the measurement signal in another frequency band, and in the second frequency band, the first antenna unit may set the level of the transmission signal to be higher than that in the another frequency band in the first frequency band.

An inspection method according to an aspect of the present disclosure is a detection method using a detection device including a first probe that includes a first antenna unit for transmission, a second probe that includes a second antenna unit for reception, the second probe being opposed to the first probe at a predetermined distance, a measurement unit that measures a measurement signal including information regarding a propagation characteristic of an electromagnetic wave in a medium between the first and second antenna units, and a calculation unit that calculates characteristics information of the medium on the basis of a characteristic amount obtained from the measurement signal, and includes, in a first mode, measuring the measurement signal in a first frequency band for the electromagnetic wave propagating in the medium, and calculating the characteristics information of the medium on the basis of a first characteristic amount obtained from the measurement signal in the first frequency band, and, in a second mode, measuring the measurement signal in a second frequency band, which is a part of the first frequency band for the electromagnetic wave, and calculating the characteristics information of the medium on the basis of a second characteristic amount obtained from the measurement signal in the second frequency band.

In the first mode, the calculation unit may generate relationship information between the first characteristic amount and a partial characteristic amount on the basis of the partial characteristic amount obtained from the measurement signal in the second frequency band out of the measurement signal in the first frequency band, and in the second mode, the calculation unit may calculate the characteristics information of the medium by applying the second characteristic amount to the relationship information.

The second frequency band may be a band including a peak frequency at which an intensity of the measurement signal in the first frequency band is maximum.

In the first mode, the measurement unit may measure the electromagnetic wave at a first frequency spacing, and in the second mode, the measurement unit may measure the electromagnetic wave at a second frequency spacing wider than the first frequency spacing.

A width of the second frequency band may be substantially equal to a width of the first frequency band.

The second frequency band may be a specific frequency in the first frequency band.

The characteristic amount may be a propagation delay time of the electromagnetic wave between the first and second antenna units, a shape of a frequency characteristic of the electromagnetic wave, or a waveform of the propagation delay time obtained on the basis of the frequency characteristic of the electromagnetic wave.

The characteristic amount may be a phase or an amplitude of the electromagnetic wave at the specific frequency.

In the first mode, the calculation unit may calculate a first propagation delay time on the basis of the measurement signal in the first frequency band, calculate a partial delay time obtained from the measurement signal in the second frequency band out of the measurement signal in the first frequency band, and generate the relationship information using the first propagation delay time and the partial delay time, and in the second mode, the calculation unit may calculate a second propagation delay time on the basis of the measurement signal in the second frequency band, generate a corrected delay time obtained by converting the second propagation delay time into a propagation delay time in the first frequency band by applying the second propagation delay time to the relationship information, and calculate a relative permittivity of the medium and a water content in the medium using the corrected delay time.

In the second frequency band, an upper limit of a level of the transmission signal out of the first frequency band may be higher than an upper limit of a level of the measurement signal in another frequency band, and in the second frequency band, the first antenna unit may set the level of the transmission signal to be higher than that in the another frequency band in the first frequency band.

MODE FOR CARRYING OUT THE INVENTION

Hereinafter, specific embodiments to which the present technology has been applied will be described in detail with reference to the drawings. The drawings are schematic or conceptual, and the ratio or the like of respective components is not necessarily the same as actual one. In the description and the drawings, similar components to those that have been described with reference to the previously described drawings are labeled with the same reference signs, and the detailed description thereof is omitted as needed.

EMBODIMENT

Figure 1:
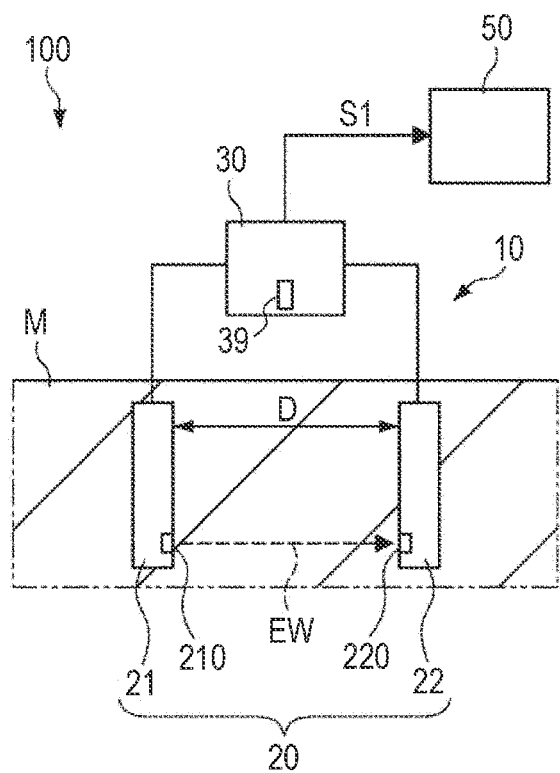
FIG. 1 is a schematic configuration diagram of a measurement device including a water content measurement sensor according to an embodiment.
Figure 2:
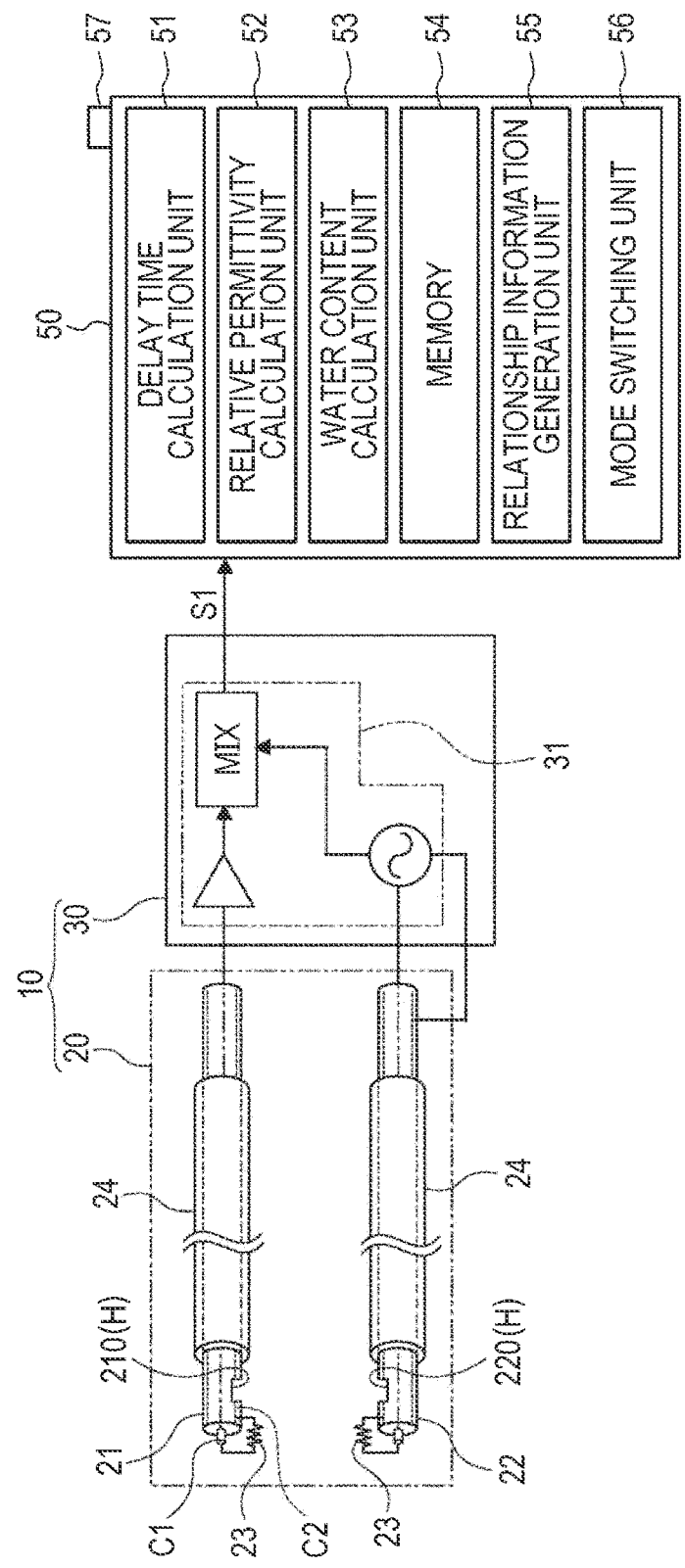
FIG. 2 is a block diagram illustrating a configuration of the water content measurement sensor.

FIG. 1 is a schematic configuration diagram of a measurement device including a water content measurement sensor according to an embodiment. FIG. 2 is a block diagram illustrating a configuration of the water content measurement sensor.

[Water Content Measurement Device]

A measurement device 100 according to the present embodiment includes a water content measurement sensor device (hereinafter, a sensor device) 10 and a signal processing unit 50. In the present embodiment, an example in which the present technology is applied to measurement of the water content of soil for growing crops will be described.

The sensor device 10 acquires an electromagnetic wave propagation characteristic of a medium (soil) M and generates a measurement signal S1 used for calculating the relative permittivity of the medium M. The signal processing unit 50 receives the measurement signal S1 from the sensor device 10 and calculates the water content in the medium M on the basis of the measurement signal S1.

Hereinafter, details of each unit will be described.

The sensor device 10 includes a sensor head 20 and a measurement unit 30.

(Sensor Head)

The sensor head 20 includes a transmission probe 21 (first probe) and a reception probe 22 (second probe). The sensor head 20 is arranged in the medium M such as soil, and the transmission and reception probes 21 and 22 respectively include antenna units 210 and 220 (a first antenna unit and a second antenna unit) capable of transmitting and receiving an electromagnetic wave EW of a predetermined frequency between the transmission and reception probes 21 and 22.

The transmission probe 21 and the reception probe 22 are buried in the medium M in substantially vertical postures so as to be opposed to each other at a distance D. Each of the transmission probe 21 and the reception probe 22 is a coaxial cable including a core wire portion C1 and a shield portion C2. The thickness and length of the cable are not particularly limited, and may be any thickness and length. For example, by setting the thickness (diameter) of the cable to 2 mm to 6 mm, the cable can easily be inserted into the soil. The core wire portion C1 includes a copper wire, and the shield portion C2 includes a copper pipe. However, the shield portion C2 may include a mesh body of a copper wire. The outer surface of the shield portion C2 is covered with a protective layer including an insulating material although the protective layer is not illustrated.

The transmission probe 21 is connected to an output terminal 34 (see FIG. 3) of the measurement unit 30, and transmits a transmission signal from the measurement unit 30 to the antenna unit 210. The antenna unit 210 is provided at or near the tip end portion (terminal portion) of the transmission probe 21, and transmits the electromagnetic wave EW corresponding to the transmission signal to the reception probe 22.

The reception probe 22 is connected to an input terminal 35 (see FIG. 3) of the measurement unit 30, receives the electromagnetic wave EW at the antenna unit 220, and inputs a reception signal to the measurement unit 30. The antenna unit 220 is provided at or near the tip end portion (terminal portion) of the reception probe 22 so as to be opposed to the antenna unit 210 of the transmission probe 21. The antenna units 210 and 220 do not have to be provided at the tip end portions of the probes 21 and 22, but may be provided at arbitrary positions such as the center positions of the probes 21 and 22.

The antenna units 210 and 220 are configured to locally transmit and receive the electromagnetic wave EW at predetermined positions of the probes 21 and 22, and typically include minute antennae formed in sizes that do not cause the probes 21 and 22 to resonate. With this arrangement, a decrease in measurement accuracy due to the resonance of the probes 21 and 22 can be suppressed.

In the present embodiment, each of the antenna units 210 and 220 includes an opening portion H provided in a part of the shield portion C2. That is, each of the probes 21 and 22 includes a leaky coaxial antenna having each of the antenna units 210 and 220 as a radio wave leakage unit.

The opening portion H is formed in an opening shape such as a rectangular shape, a circular shape, an elliptical shape, and an oval shape. In the present embodiment, the opening portion H is formed in an oval shape having a long axis in the longitudinal direction of each of the probes 21 and 22. The length of the long axis of the opening portion H can appropriately be set in accordance with the wavelength of the electromagnetic wave EW to be used. For example, in a case where the wavelength of the electromagnetic wave EW is 1 GHz to 9 GHz, the length of the long axis of the opening portion H is about 5 mm to 15 mm.

Each of the transmission probe 21 and the reception probe 22 includes a termination resistor 23. The termination resistor 23 is electrically connected between the termination portion of the core wire portion C1 and the shield portion C2. Thus, unnecessary reflection of the transmission or reception signal at the probe termination is prevented.

The tip end portions of the transmission probe 21 and the reception probe 22 are desirably covered with electromagnetic wave transmitting protection members (not illustrated) covering the antenna units 210 and 220.

Each of the transmission probe 21 and the reception probe 22 further includes a sleeve 24 containing an electromagnetic wave absorbing material. The sleeves 24 cover the outer peripheral surfaces of the probes 21 and 22 around the antenna units 210 and 220 (opening portions H) to suppress leakage of transmission and reception signals from regions other than the opening portions H.

Ferrite is mainly used as the electromagnetic wave absorbing material constituting the sleeve 24, but the present disclosure is not limited thereto, and other high magnetic permeability materials such as sendust and permalloy may be used in accordance with the frequency of the electromagnetic wave EW and the like. The sleeves 24 may be omitted as necessary, or the sleeve 24 may be provided only on either the probe 21 or the probe 22.

The length of the distance D between the transmission probe 21 and the reception probe 22 is not particularly limited, and is, for example, 20 mm to 100 mm. In a case where the distance D is longer than 100 mm, the attenuation of the electromagnetic wave EW propagating through the medium M becomes significant, and there is a possibility that sufficient reception intensity cannot be obtained. On the other hand, in a case where the distance D is shorter than 20 mm, it is technically difficult to observe the electromagnetic wave EW. In addition, in a case where the distance D is short, a gap formed in the vicinity of the probes 21 and 22 has a large effect, and there is a possibility that the correct relative permittivity or water content cannot be measured.

The gap described above is an air layer formed between the medium M and the surroundings of the probes 21 and 22, and is formed when the probes 21 and 22 are buried in the medium M from the surface thereof or when the probes 21 and 22 are moved in the medium M. As will be described later, in order to accurately measure the relative permittivity or the water content of the medium M, the size of the gap (thickness of the air layer) is preferably small, but typically, a gap of about 1 mm may be generated.

(Measurement Unit)

Figure 3:
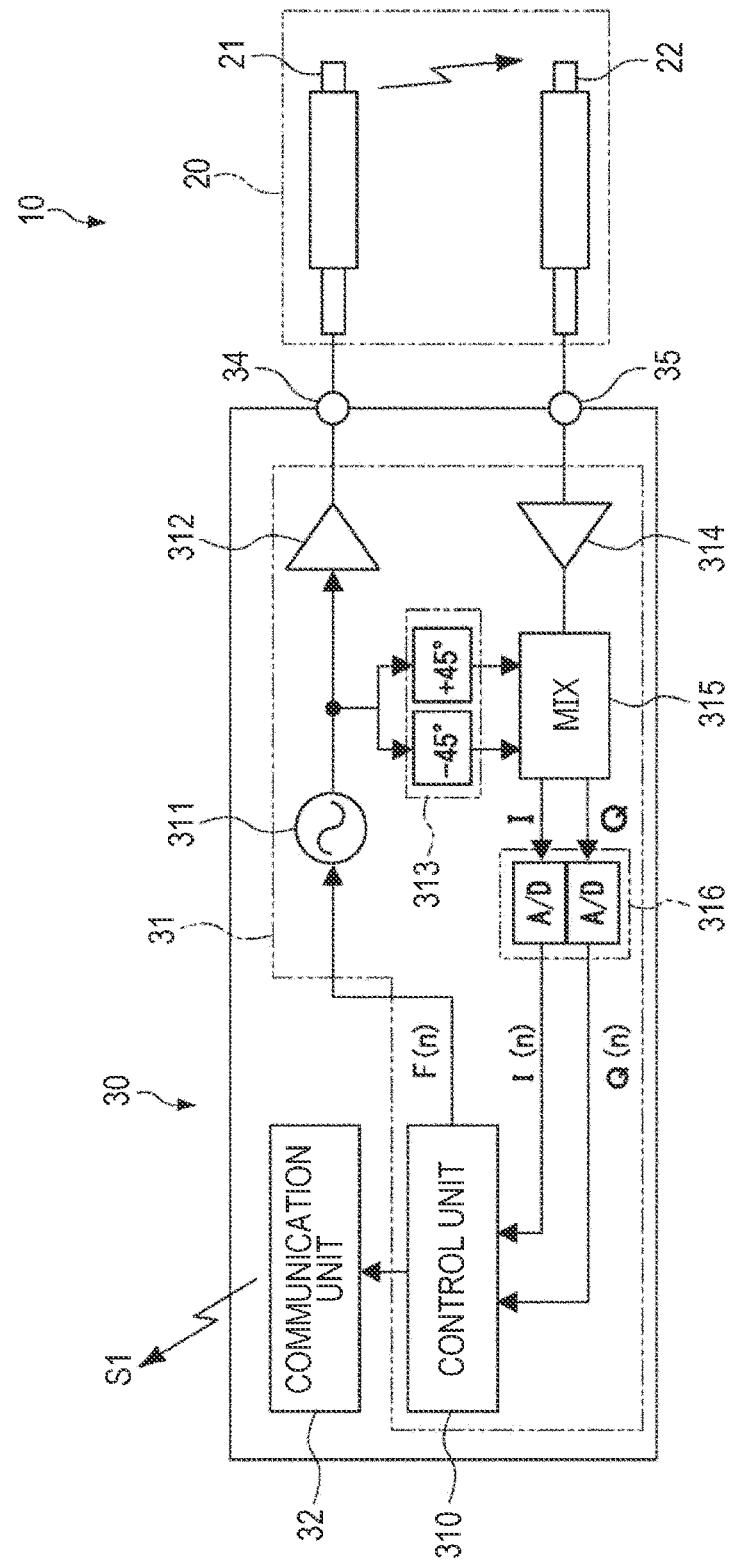
FIG. 3 is a block diagram illustrating a configuration of a measurement unit.

FIG. 3 is a block diagram illustrating a configuration of the measurement unit.

The measurement unit 30 includes a signal generation unit 31 and a communication unit 32. The measurement unit 30 typically includes a network analyzer.

The signal generation unit 31 includes a control unit 310, a signal generator 311, a phase shifter 313, a mixer 315, and the like. The signal generation unit 31 generates the measurement signal S1 including information regarding a propagation characteristic of the electromagnetic wave EW in the medium M between the antenna unit 210 of the transmission probe 21 and the antenna unit 220 of the reception probe 22.

The control unit 310 includes a computer having a central processing unit (CPU), a memory, and the like, and controls each unit of the measurement unit 30 including the signal generator 311 and the communication unit 32.

The signal generator 311 generates a transmission signal F having a predetermined frequency and inputs the transmission signal F into the transmission probe 21 via an amplifier 312 and the output terminal 34. The signal generator 311 generates a pulse wave (pulse signal) as the transmission signal F, but may be configured to generate a continuous wave as the transmission signal F.

The signal generator 311 may have a frequency sweep function for the transmission signal F. In this case, the signal generator 311 generates the transmission signal F of, for example, 1 GHz to 9 GHz on the basis of a command from the control unit 310.

The phase shifter 313 separates the transmission signal F into two signals having phases different by 90 degrees and inputs the two signals into the mixer 315. The mixer 315 mixes a reception signal input from the reception probe 22 via the input terminal 35 and an amplifier 314 with the two signals output from the phase shifter 313, and modulates the reception signal into two response signals (an I signal and a Q signal) orthogonal to each other. These response signals are converted from analog signals to digital signals via an AD converter 316 and generated as the measurement signal S1 in the control unit 310.

The phase shifter 313 and the mixer 315 constitute a detector that performs quadrature detection (IQ detection) on the output of the reception probe 22. The sum of squares of the I signal and the Q signal corresponds to the intensity of the reception signal, the square root of the sum of squares of the I signal and the Q signal corresponds to the amplitude of the reception signal, and the arctangent of the I signal and the Q signal corresponds to the phase.

The communication unit 32 includes a communication module including a communication antenna and the like. The communication unit 32 is configured to wirelessly transmit the measurement signal S1 from the sensor device 10 to the signal processing unit 50. Therefore, the measurement signal S1 can be provided to the signal processing unit 50 arranged at a different site from the observation site. The present disclosure is not limited thereto, and the sensor device 10 may be connected to the signal processing unit 50 via a wiring cable or the like.

(Signal Processing Unit)

As illustrated in FIG. 2, the signal processing unit 50 as a calculation unit includes a delay time calculation unit 51, a relative permittivity calculation unit 52, a water content calculation unit 53, a memory 54, a relationship information generation unit 55, and mode switching units 56 and 57. The signal processing unit 50 includes an information processing device that obtains a characteristic amount such as a propagation delay time of the electromagnetic wave EW on the basis of the measurement signal S1 transmitted from the sensor device 10 (measurement unit 30), and further calculates characteristics information such as a water content in the medium M from the characteristic amount.

The information processing device can be fulfilled by hardware elements used for a computer, such as a CPU, a random access memory (RAM), and a read only memory (ROM), and necessary software. Instead of or in addition to the CPU, a programmable logic device (PLD) such as a field programmable gate array (FPGA), a digital signal processor (DSP), an application specific integrated circuit (ASIC), or the like may be used.

In the present embodiment, the CPU executes a predetermined program to cause the delay time calculation unit 51, the relative permittivity calculation unit 52, the water content calculation unit 53, the relationship information generation unit 55, and the mode switching unit 56 as functional blocks to be fulfilled. The RAM or the like of the signal processing unit 50 constitutes the memory 54. Of course, dedicated hardware such as an integrated circuit (IC) may be used to fulfill each block. The program is installed in the signal processing unit 50 via various recording media, for example. Alternatively, the program may be installed via the Internet or the like.

The delay time calculation unit 51 is configured to calculate as a characteristic amount a propagation delay time of the electromagnetic wave EW between the transmission probe 21 (antenna unit 210) and the reception probe 22 (antenna unit 220) on the basis of the measurement signal S1.

The propagation delay time of the electromagnetic wave EW refers to a difference between the propagation time of the electromagnetic wave EW in the air and the propagation time of the electromagnetic wave EW in the medium M. The propagation delay time of the electromagnetic wave depends on the relative permittivity of the transmission path, and the propagation delay time is proportional to the square root of the relative permittivity of the medium. In general, the relative permittivity of the soil itself is about 1 to 10, and changes depending on the water content. Therefore, if the propagation delay time can be measured, the water content in the medium M can indirectly be measured.

A method of calculating the propagation delay time is not particularly limited, and in the present embodiment, the measurement signal S1 is subjected to inverse Fourier transform (inverse FFT) to derive an impulse response, and a pulse delay time is calculated from the peak position of the impulse response. The propagation delay time of the electromagnetic wave EW is calculated by subtracting a transmission time (cable transmission time) through the probes 21 and 22 from the pulse delay time.

The relative permittivity calculation unit 52 is configured to calculate as characteristics information of the medium M the relative permittivity of the medium M on the basis of the propagation delay time of the electromagnetic wave EW calculated in the delay time calculation unit 51. The relative permittivity of water is typically 80.

The water content calculation unit 53 is configured to calculate the water content in the medium M on the basis of the relative permittivity calculated in the relative permittivity calculation unit 52. For the calculation of the water content, for example, the Topp equation is used (described later), and the volumetric water content [%] of the medium M is calculated as the water content. Alternatively, the water content calculation unit 53 may calculate the water content directly from the propagation delay time of the electromagnetic wave EW without obtaining the relative permittivity.

The relationship information generation unit 55 generates relationship information between a propagation delay time DL11 obtained using the measurement signal in a certain frequency band (first frequency band) and a partial delay time DL12 obtained using the measurement signal in a frequency band (second frequency band), which is a part of the first frequency band. The relationship information may be a function or a correspondence table representing a relationship between the propagation delay time DL11 and the partial delay time DL12. This relationship information is stored in the memory 54.

The mode switching units 56 and 57 switch between a first mode and a second mode to be described later. For example, in the first mode, the measurement unit 30 measures the measurement signal in the first frequency band for the electromagnetic wave EW propagating through the medium M. That is, the measurement unit 30 measures the measurement signal for the electromagnetic wave EW propagating through the medium M while changing the frequency of the electromagnetic wave EW at predetermined spacings (first frequency spacing) within the first frequency band. The signal processing unit 50 calculates the relative permittivity and the water content of the medium M on the basis of the first propagation delay time (first characteristic amount) DL11 obtained from the measurement signal in the first frequency band. At the same time, the signal processing unit 50 extracts the measurement signal part in the second frequency band to be used in the second mode from the measurement signal obtained in the first mode, and derives the partial delay time (partial characteristic amount) DL12 from the measurement signal part. The second frequency band is a partial frequency band in the first frequency band or a specific frequency in the first frequency band. For example, the second frequency band may be a band including a peak frequency, in which the measurement signal has the maximum intensity in the first frequency band, in order to accurately detect the measurement signal. Further, the signal processing unit 50 derives relationship information (for example, a relational expression or a correspondence table) between the first propagation delay time DL11 and the partial delay time DL12. Note that generation of the relationship information will be described later. Also, as described later, the characteristic amount is not limited to the propagation delay time.

In the second mode, the measurement unit 30 measures the measurement signal in the second frequency band for the electromagnetic wave EW propagating through the medium M. The signal processing unit 50 calculates the relative permittivity and the water content of the medium M on the basis of a second propagation delay time DL22 obtained from the measurement signal in the second frequency band. In the second mode, the signal processing unit 50 calculates a corrected delay time DL21 by applying the second propagation delay time DL22 obtained in the second mode to the relationship information calculated in the first mode. For example, in a case where the relationship information is a relational expression representing the relationship between the first propagation delay time DL11 and the partial delay time DL12, the signal processing unit 50 substitutes the second propagation delay time DL22 obtained in the second mode for the partial delay time DL12 in the relational expression. The first propagation delay time DL11 thus obtained is defined as the corrected delay time DL21. The corrected delay time DL21 corresponds to a propagation delay time obtained using the first frequency band. That is, the signal processing unit 50 can convert (correct) the second propagation delay time DL22 into the propagation delay time (DL21) in the first frequency band by applying the second propagation delay time DL22 to the aforementioned relational expression. The signal processing unit 50 calculates the relative permittivity or the water content using the corrected delay time DL21 corrected in this manner.

In a case where the relationship information is a correspondence table representing the relationship between the first propagation delay time DL11 and the partial delay time DL12, the signal processing unit 50 is only required to convert the second propagation delay time DL22 obtained in the second mode into the corrected delay time DL21 with reference to the correspondence table. For example, the signal processing unit 50 is only required to search the correspondence table for a partial delay time DL12 equal to or closest to the second propagation delay time DL22 and set the first propagation delay time DL11 corresponding to the partial delay time DL12 as the corrected delay time DL21.

Alternatively, the signal processing unit 50 may perform interpolation using a plurality of partial delay times DL12 close to the second propagation delay time DL22, and set the first propagation delay time DL11 corresponding to the interpolated value as the corrected delay time DL21.

As described above, in the first mode, the signal processing unit 50 according to the present disclosure generates the relationship information between the first propagation delay time DL11 in the first frequency band and the partial delay time DL12 in the second frequency band. In the second mode, the signal processing unit 50 converts the second propagation delay time DL22 into the propagation delay time (corrected delay time DL21) in the first frequency band by applying the second propagation delay time DL22 in the second frequency band to the relationship information described above. Therefore, in the second mode, the propagation delay time in the first frequency band can be estimated while using the second frequency band, which is a part of the first frequency band. Thereafter, the signal processing unit 50 calculates the relative permittivity or the water content using the corrected delay time DL21.

The mode switching units 56 and 57 are switches that switch between these first mode and the second mode. The mode switching unit 56 is, for example, a switch function (software) provided in the signal processing unit 50. The mode switching unit 57 is, for example, a physical switch provided on the housing of the sensor device 10. The mode switching unit 56 is used in a case where mode switching is automatically executed inside the signal processing unit 50. The mode switching unit 57 is used in a case where the user arbitrarily executes mode switching. The sensor device 10 may include both or one of the mode switching units 56 and 57.

The signal processing unit 50 may further include a communication unit configured to be able to communicate with the communication unit 32 of the measurement unit 30, a display unit capable of displaying information regarding the propagation delay time, the relative permittivity, the water content, and the like calculated in each functional block, and the like.

Here, in the first mode, since the measurement unit 30 measures the electromagnetic wave EW in the relatively wide first frequency band, the resolution is high, and the water content can be calculated accurately. However, in a case where the measurement is performed only in the first mode, it takes a relatively long time, and power consumption is high. In the second mode, since the measurement unit 30 measures the electromagnetic wave EW in the second frequency band, which is a part of the first frequency band, it takes only a relatively short time, and power consumption is low. However, in a case where the measurement is performed only in the second mode, the resolution is low, and it is difficult to calculate the water content accurately.

Under such circumstances, in the present embodiment, for example, relationship information is initially generated in the first mode in order to obtain the relationship information described above, and then the measurement is executed in the second mode using the relationship information. As a result, in the first mode, a relatively long time and high power consumption are required, but in the subsequent second mode, measurement can be repeated in a short time and with low power consumption. Also, in the second mode, the signal processing unit 50 converts the second propagation delay time DL22 into the corrected delay time DL21 corresponding to the propagation delay time in the first frequency band by using the relationship information obtained in the wide first frequency band. Therefore, in the inspection device according to the present embodiment, measurement can be executed in a short time and with low power consumption, and a relatively accurate water content comparable to that obtained in measurement in the first frequency band can be obtained.

(Water Content Measurement Method)

Hereinafter, the operation of the water content measurement device according to the present embodiment will be described for the details of the signal processing unit 50.

(First Mode)

Figure 4:
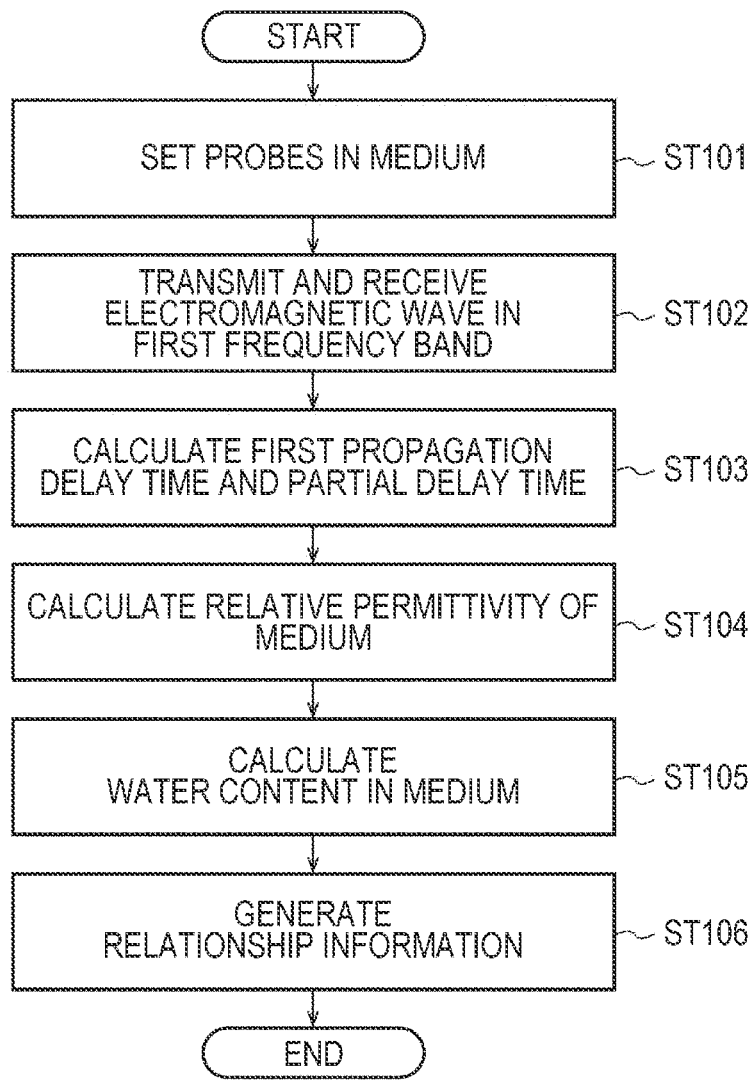
FIG. 4 is a flowchart describing a water content measurement method and a relationship information generation method in a first mode.
Figure 5A:
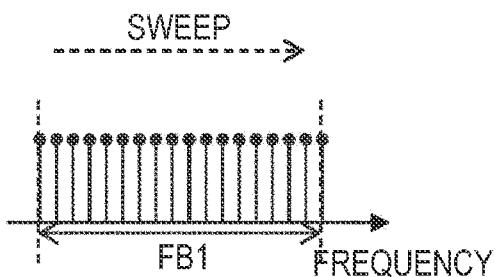
FIG. 5A is a diagram illustrating the signal level at the time of transmission of an electromagnetic wave in a first frequency band.
Figure 5B:
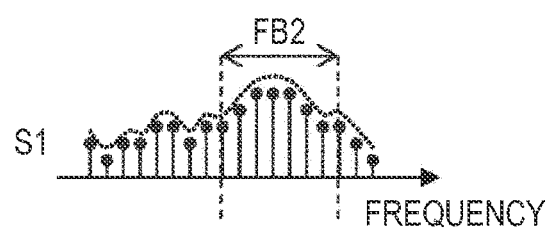
FIG. 5B is a diagram illustrating the level of a measurement signal of the electromagnetic wave in the first frequency band.
Figure 5C:
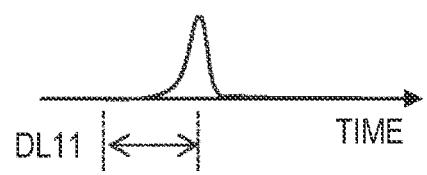
FIG. 5C is a diagram illustrating a first propagation delay time.
Figure 5D:
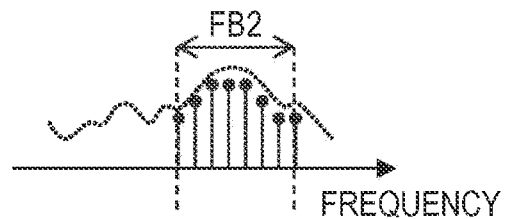
FIG. 5D is a diagram illustrating the level of the measurement signal of the electromagnetic wave in a second frequency band.
Figure 5E:
FIG. 5E is a diagram illustrating a partial delay time.

FIG. 4 is a flowchart describing a water content measurement method and a relationship information generation method in the first mode. FIG. 5A is a diagram illustrating the signal level at the time of transmission of the electromagnetic wave EW in the first frequency band. FIG. 5B is a diagram illustrating the level of the measurement signal of the electromagnetic wave EW in the first frequency band. FIG. 5C is a diagram illustrating the first propagation delay time DL11. FIG. 5D is a diagram illustrating the level of the measurement signal of the electromagnetic wave EW in the second frequency band. FIG. 5E is a diagram illustrating the partial delay time DL12.

First, as illustrated in FIG. 1, the transmission probe 21 and the reception probe 22 are buried in the soil M (step 101). The opposed distance D between the transmission probe 21 and the reception probe 22 is, for example, 50 mm.

Subsequently, the electromagnetic wave EW is transmitted and received between the transmission probe 21 (antenna unit 210) and the reception antenna (antenna unit 220) (step 102). At this time, the measurement unit 30 generates the measurement signal S1 including the orthogonal frequency response signals (the I(n) signal and the Q(n) signal) of the reception signal output from the reception probe 22 while changing the frequency of the transmission signal F(n) input into the transmission probe 21 in steps of 50 MHz. As illustrated in FIG. 5A, the measurement unit 30 changes and sweeps the frequency of the electromagnetic wave EW in the first frequency band FB1 in steps of 10 MHz. Therefore, as illustrated in FIG. 5B, the measurement signal S1 in the first frequency band FB1 is obtained. The measurement signal S1 is transmitted to the signal processing unit 50.

Subsequently, the signal processing unit 50 (delay time calculation unit 51) calculates the first propagation delay time DL11 of the electromagnetic wave EW between the transmission probe 21 and the reception probe 22 on the basis of the measurement signal S1 (step 103). Here, as illustrated in FIG. 5C, the delay time calculation unit 51 calculates the first propagation delay time DL11 using the measurement signal S1 in the first frequency band FB1. At the same time, the delay time calculation unit 51 extracts a measurement signal in the second frequency band FB2, which is a part of the first frequency band FB1, as illustrated in FIG. 5D, and calculates the partial delay time DL12 using the measurement signal in the second frequency band FB2 as illustrated in FIG. 5E. That is, the delay time calculation unit 51 generates the first propagation delay time DL11 and generates the partial delay time DL12 using the measurement signal S1 in the first mode. The second frequency band FB2 may be a partial frequency band in the measurement signal S1 in the first mode, in which a propagation loss is small, and in which a large signal intensity can be obtained. Since the second frequency band FB2 is set to be a frequency band with a small propagation loss, the measurement unit 30 can reliably detect a measurement signal S2 in the second frequency band FB2 in the second mode. Furthermore, the signal-to-noise ratio (SN ratio) of the measurement signal S2 in the second mode is improved. This leads to suppression of the power of the transmission signal in the second mode.

The propagation delay time, and the relative permittivity and water content of the medium M are calculated as follows. Note that the first propagation delay time DL11 is calculated using the first frequency band FB1 for the measurement signal S1, and the partial delay time DL12 is calculated using the second frequency band FB2 out of the measurement signal S1.

The delay time calculation unit 51 performs inverse Fourier transform (IFFT) on the reception signal by fast Fourier transform using the I(n) signal as a real part and the Q(n) signal as an imaginary part to derive an impulse response $h(\tau)$.

$$h(\tau)=\text{IFFT}\{I(n), Q(n)\} \quad \text{(Equation 1)}$$

The delay time calculation unit 51 derives a pulse delay time $\tau$ [s] from the peak position of the impulse response $h(\tau)$ and subtracts a cable transmission time $\tau_0$ [s] from the pulse delay time $\tau$ to derive a propagation delay time $\tau_{delay}$ [s].

$$\tau_{delay}=\tau-\tau_0 \quad \text{(Equation 2)}$$

Subsequently, the signal processing unit 50 (relative permittivity calculation unit 52) calculates relative permittivity $\varepsilon_r$ of the medium M with the propagation delay time DL11 or DL12 as $\tau_{delay}$ [s], the light speed as c [m/s], and the inter-probe distance (D) as d [m] (step 104).

$$\tau_{delay}=d\cdot\sqrt{(\varepsilon_r)}/c \quad \text{(Equation 3)}$$

Subsequently, the signal processing unit 50 (water content calculation unit 53) calculates a water content (volumetric water content) $\theta$[%] in the medium M from the Topp equation (step 105).

$$\theta=-5.3\times10^{-2}+2.92\times10^{-2}\varepsilon_r-5.5\times10^{-4}\varepsilon_r^2+4.3\times10^{-6}\varepsilon_r^3 \quad \text{(Equation 4)}$$

In this manner, the propagation delay times DL11 and DL12, and the relative permittivity and water content of the medium M can be calculated using the above Equations 1 to 4.

Subsequently, the signal processing unit 50 (relationship information generation unit 55) generates relationship information between the first propagation delay time DL11 and the partial delay time DL12 (step 106).

Figure 6:
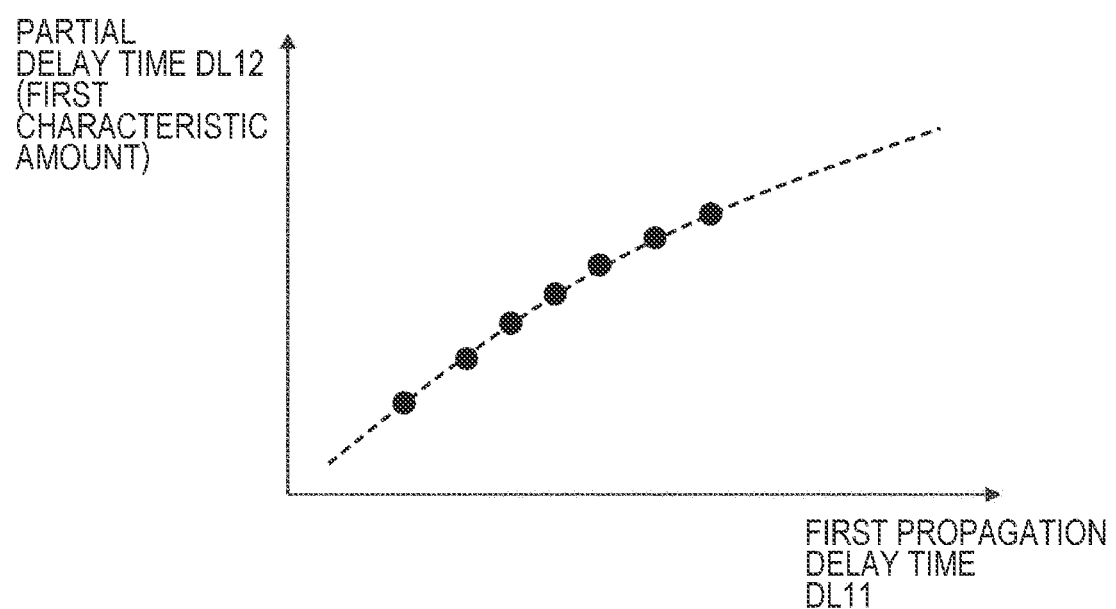
FIG. 6 is a graph illustrating a relationship between the first propagation delay time and the partial delay time.

For example, FIG. 6 is a graph illustrating a relationship between the first propagation delay time DL11 and the partial delay time DL12. By repeating steps 102 to 105, the graph as illustrated in FIG. 6 is obtained. As a result, a relational expression between the first propagation delay time DL11 and the partial delay time DL12 is obtained. The relational expression may be a linear function or a quadratic or higher function. The relational expression is stored in the memory 54. Note that the relationship information may be a correspondence table representing the relationship between the first propagation delay time DL11 and the partial delay time DL12.

In this manner, in the first mode, the first propagation delay time DL11 is calculated using the measurement signal in the wide first frequency band FB1, and the relative permittivity of the medium M and the volumetric water content (water content) in the medium M are calculated using the first propagation delay time DL11. At the same time, the relationship information between the first propagation delay time DL11 in the first frequency band FB1 and the partial delay time DL12 in the second frequency band FB2 is generated.

(Second Mode)

Figure 7:
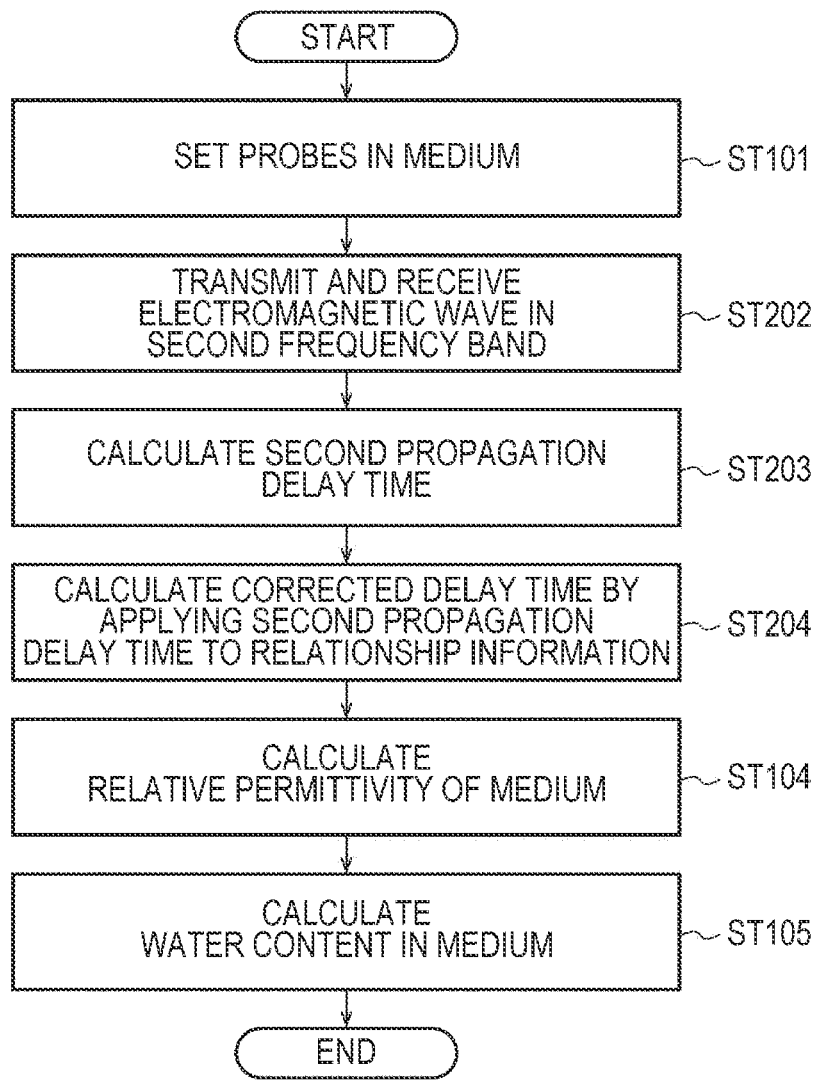
FIG. 7 is a flowchart describing a water content measurement method in a second mode.
Figure 8A:
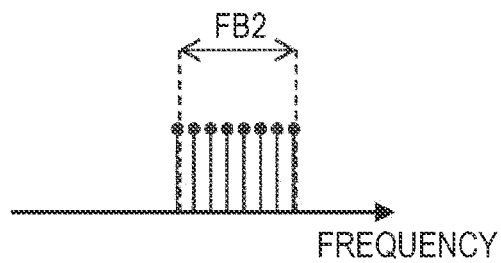
FIG. 8A is a diagram illustrating the signal level at the time of transmission of the electromagnetic wave in the second frequency band.
Figure 8B:
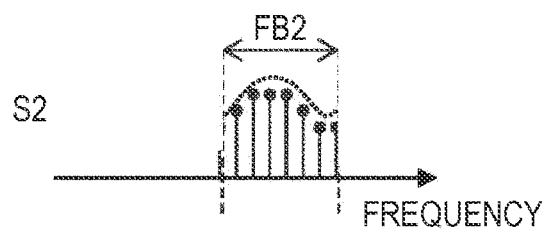
FIG. 8B is a diagram illustrating the level of the measurement signal of the electromagnetic wave in the second frequency band.
Figure 8C:
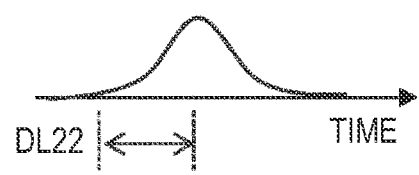
FIG. 8C is a diagram illustrating a second propagation delay time.
Figure 8D:
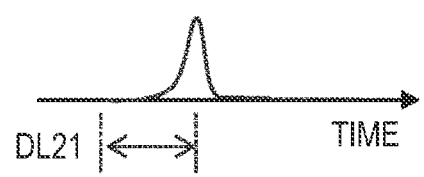
FIG. 8D is a diagram illustrating a corrected delay time.

FIG. 7 is a flowchart describing a water content measurement method in the second mode. FIG. 8A is a diagram illustrating the signal level at the time of transmission of the electromagnetic wave EW in the second frequency band. FIG. 8B is a diagram illustrating the level of the measurement signal of the electromagnetic wave EW in the second frequency band. FIG. 8C is a diagram illustrating the second propagation delay time DL22. FIG. 8D is a diagram illustrating the corrected delay time DL21.

First, as in the first mode, step 101 is performed. Therefore, the transmission probe 21 and the reception probe 22 are buried in the soil M.

Subsequently, the electromagnetic wave EW is transmitted and received between the transmission probe 21 (antenna unit 210) and the reception antenna (antenna unit 220) (step 202). At this time, as illustrated in FIG. 8A, the measurement unit 30 changes and sweeps the frequency of the electromagnetic wave EW in the second frequency band FB2 in steps of 50 MHz. Therefore, as illustrated in FIG. 8B, the measurement signal S2 in the second frequency band FB2 is obtained. The measurement signal S2 is transmitted to the signal processing unit 50.

Subsequently, as illustrated in FIG. 8C, the delay time calculation unit 51 calculates the second propagation delay time DL22 of the electromagnetic wave EW between the transmission probe 21 and the reception probe 22 on the basis of the measurement signal S2 (step 203). Similarly to the propagation delay times DL11 and DL12, the second propagation delay time DL22 can be calculated using Equations 1 and 2 described above. The second propagation delay time DL22 is calculated using the measurement signal S2 in the second frequency band FB2.

Subsequently, as illustrated in FIG. 8D, the delay time calculation unit 51 calculates the corrected delay time DL21 by applying the second propagation delay time DL22 to the relationship information obtained in the first mode (step 204). For example, the delay time calculation unit 51 calculates the corrected delay time DL21 by substituting the second propagation delay time DL22 for the partial delay time DL12 in the aforementioned relational expression. The corrected delay time DL21 corresponds to the first propagation delay time DL11 in a case where the second propagation delay time DL22 is substituted for the partial delay time DL12. Therefore, the corrected delay time DL21 is a propagation delay time obtained by correcting the second propagation delay time DL22 so as to correspond to the propagation delay time in the first frequency band. Hence, although the corrected delay time DL21 is calculated using the measurement signal S2 in the second frequency band, the corrected delay time DL21 is a corrected and relatively accurate propagation delay time.

Note that, in a case where the relationship information is a correspondence table between the first propagation delay time DL11 and the partial delay time DL12, the delay time calculation unit 51 searches the correspondence table for a partial delay time DL12 equal to or closest to the second propagation delay time DL22. Then, the delay time calculation unit 51 is only required to set the first propagation delay time DL11 corresponding to the partial delay time DL12 hit in the search as the corrected delay time DL21. Alternatively, the delay time calculation unit 51 may perform interpolation using a plurality of partial delay times DL12 close to the second propagation delay time DL22, and set the first propagation delay time DL11 corresponding to the interpolated value as the corrected delay time DL21. In this manner, the delay time calculation unit 51 converts the second propagation delay time DL22 into the corrected delay time DL21 using the relationship information.

Subsequently, the signal processing unit 50 executes steps 104 and 105 using the corrected delay time DL21. As a result, in the second mode, the water content θ [%] in the medium M is calculated.

In this manner, in the first mode, the sensor device 10 according to the present embodiment generates the relationship information between the first propagation delay time DL11 and the partial delay time DL12 using the electromagnetic wave EW in the first frequency band, which is a relatively wide band. Thereafter, in the second mode, the sensor device 10 measures the second propagation delay time DL22 using the electromagnetic wave EW in the second frequency band, which is a part of the first frequency band, and corrects the second propagation delay time DL22 to the corrected delay time DL21 using the relationship information obtained in the first mode. As a result, initially in the first mode, a relatively long time and high power consumption are required, but subsequently in the second mode, measurement can be repeated in a short time and with low power consumption. Also, in the second mode, the signal processing unit 50 converts the second propagation delay time DL22 into the corrected delay time DL21 corresponding to the propagation delay time in the first frequency band by using the relationship information obtained in the wide first frequency band. Therefore, in the inspection device according to the present embodiment, measurement can be executed in a short time and with low power consumption, and a relatively accurate water content comparable to that obtained in measurement in the first frequency band can be obtained.

Figure 9:
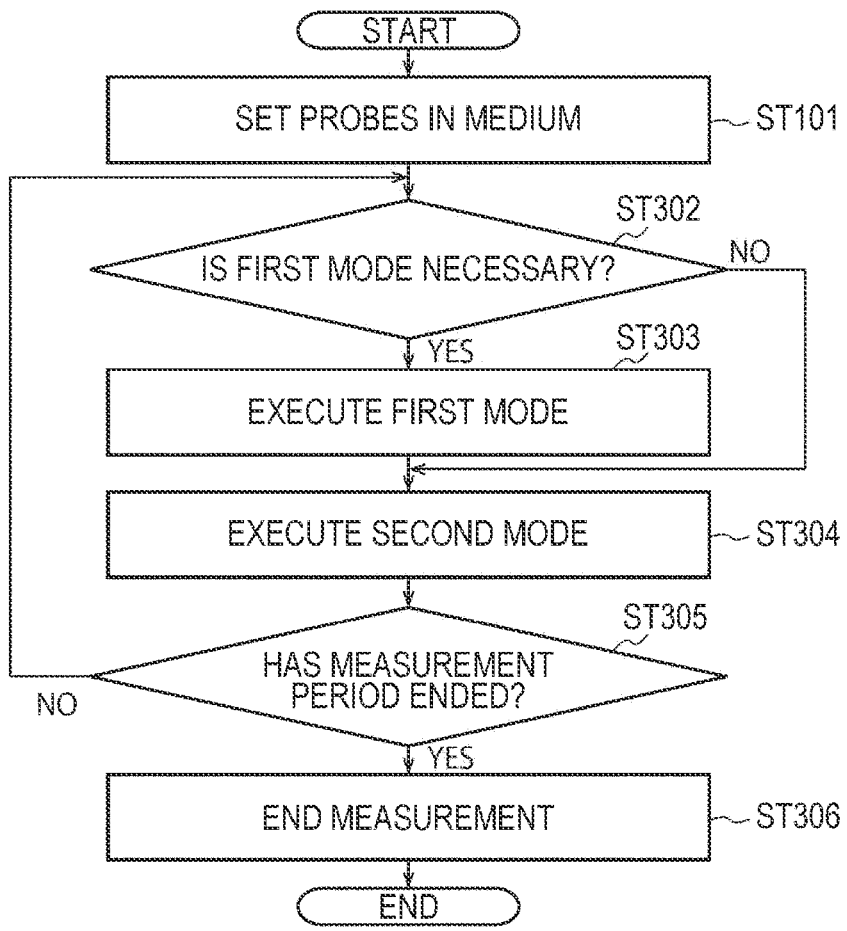
FIG. 9 is a flowchart illustrating an example of the overall operation of the sensor device in actual measurement.

FIG. 9 is a flowchart illustrating an example of the overall operation of the sensor device in actual measurement.

First, the transmission probe 21 and the reception probe 22 are buried in the soil M (step 101).

Subsequently, the signal processing unit 50 determines whether or not execution of the first mode is necessary (step 302). For example, in a case where the relationship information has not been set yet, in a case where the second mode has been executed a predetermined number of times since setting of the relationship information, in a case where a predetermined time has elapsed since setting of the relationship information, or in the like case, the signal processing unit 50 determines that it is necessary to execute the first mode (YES in step 302). In this case, the sensor device 10 performs measurement in the first mode (step 303). As a result, the relationship information is obtained. In addition, the relative permittivity and the water content of the medium M in the first mode are obtained.

On the other hand, in a case where the valid relationship information has already been set, and where it is determined that the execution of the first mode is unnecessary (NO in step 302), the sensor device 10 executes measurement in the second mode (step 304). As a result, the relative permittivity and the water content of the medium M in the second mode are also obtained.

Steps 302 to 304 are repeatedly performed for a predetermined measurement period (NO in step 305). When the measurement period ends (YES in step 305), the measurement ends (step 306). When the measurement ends, the user removes the probes 21 and 22 of the sensor device 10 from the medium M.

In this manner, the relationship information once set in the first mode may be used repeatedly in the second mode. Therefore, after generating the relationship information in the first mode, the sensor device 10 can detect the water content in the second mode with relatively high accuracy, in a short time, and with low power consumption.

Figure 10A:
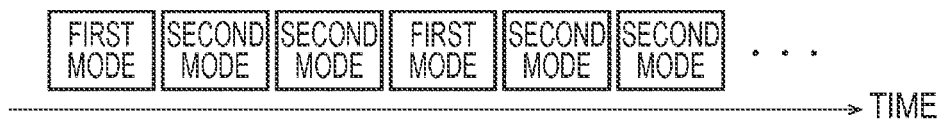
FIG. 10A is a diagram illustrating an example of the execution cycle of the first and second modes.
Figure 10B:
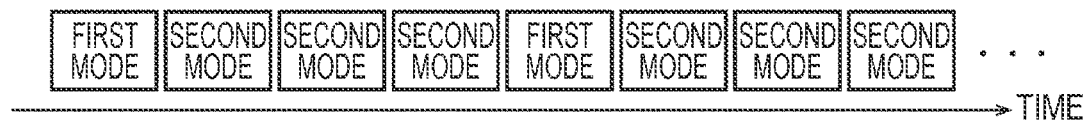
FIG. 10B is a diagram illustrating an example of the execution cycle of the first and second modes.

Meanwhile, the relationship information may periodically or arbitrarily be updated as necessary. For example, as illustrated in FIGS. 10A and 10B, the sensor device 10 may execute the first mode once every n (n≥1)-th execution of the second mode. FIGS. 10(A) and 10B are diagrams illustrating examples of the execution cycle of the first and second modes. The execution frequency of the first mode can be set by software of the mode switching unit 56. Also, the first mode may periodically be executed at predetermined intervals. In this case, the signal processing unit 50 is only required to measure the time after execution of the first mode with a not-illustrated timer. Also, the user may arbitrarily switch between the first mode and the second mode. In this case, the user is only required to arbitrarily set the mode with the mode switching unit 57, that is, the physical switch.

Furthermore, the first mode may be executed only at the time of manufacturing the sensor device 10. In this case, after the sensor device 10 is sold, the sensor device 10 performs measurement only in the second mode. Furthermore, after the sensor device 10 is sold, the sensor device 10 may execute the first mode in the first measurement, set the relationship information, and then perform measurement only in the second mode. In this manner, the first mode needs to be performed first, but needs to be performed less frequently if there is no change in the environment thereafter. However, in order to improve the measurement accuracy, the first mode is preferably performed periodically at regular intervals. Furthermore, the measurement unit 30 may include an environment sensor 39 such as a temperature sensor, and execute the first mode in accordance with a change in the environment. For example, in a case where the environment sensor 39 measures the temperature of the medium M or the air temperature, and where either of the temperatures changes by 3° C. or more, the sensor device 10 may execute the first mode to update the relationship information.

Modification Example of Second Frequency Band

In the above embodiment, the second frequency band FB2 is a band including a peak frequency at which the intensity of the measurement signal S1 in the first frequency band FB1 is maximum, and is a narrower band than the first frequency band FB1.

Figure 11A:
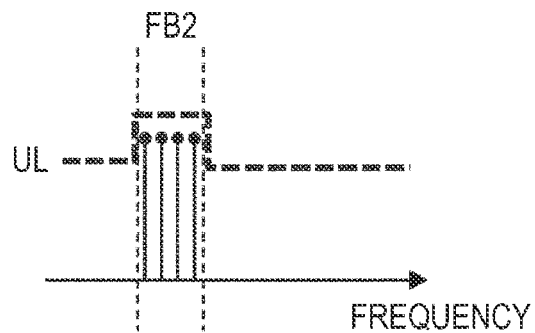
FIG. 11A is a graph illustrating a modification example of the second frequency band.
Figure 11B:
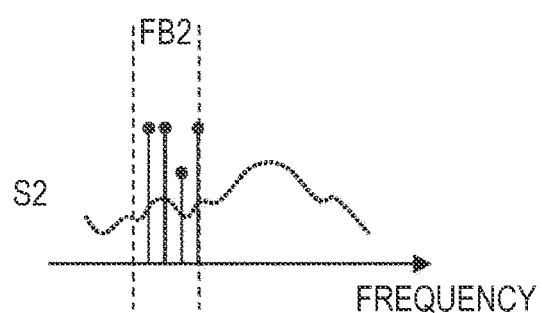
FIG. 11B is a graph illustrating the modification example of the second frequency band.
Figure 11C:
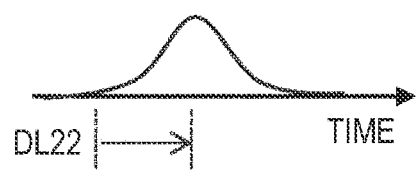
FIG. 11C is a graph illustrating the modification example of the second frequency band.

However, there is a case where the upper limit of the level of the transmission signal F of the electromagnetic wave EW is set depending on the frequency. For example, FIGS. 11A to 11C are graphs illustrating a modification example of the second frequency band. FIG. 11A illustrates the transmission signal F in the second mode. An upper limit UL of the level of the transmission signal is set. As the upper limit UL, for example, an industry science and medical (ISM) band (2.4 GHz band) may be set. In such a case, the second frequency band FB2 is only required to be set to a frequency band in which the upper limit UL of the level of the transmission signal is higher than the upper limit UL of the other frequency band. Therefore, in the second frequency band FB2, the antenna unit 210 can transmit a transmission signal at a higher level (output) than the upper limit UL of the other frequency band. Accordingly, as illustrated in FIG. 11B, in the second frequency band FB2, the measurement unit 30 can receive the measurement signal S2 at a higher level than the measurement signal in the other frequency band. In a case where the level of the measurement signal S2 is high, the measurement unit 30 can accurately detect the measurement signal S2 even in a noisy environment. Since the signal processing unit 50 calculates the second propagation delay time DL22 and the corrected delay time DL21 using the frequency band having a high signal level, the signal processing unit 50 is hardly affected by noise, and can detect an accurate water content.

Figure 12A:
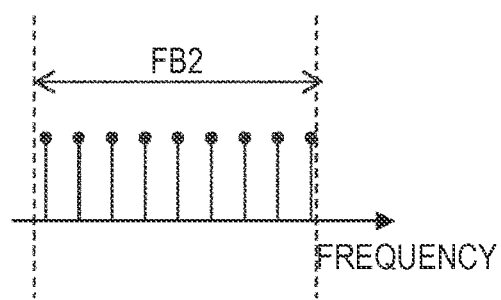
FIG. 12A is a graph illustrating another modification example of the second frequency band.
Figure 12B:
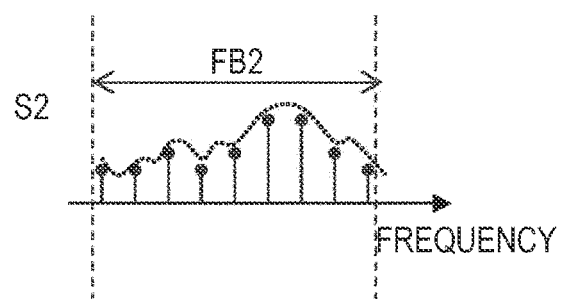
FIG. 12B is a graph illustrating the modification example of the second frequency band.
Figure 12C:
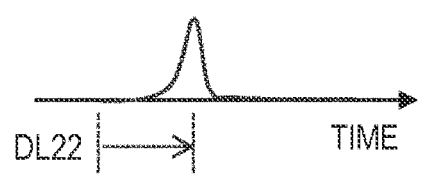
FIG. 12C is a graph illustrating the modification example of the second frequency band.

FIGS. 12A to 12C are graphs illustrating another modification example of the second frequency band. In FIG. 12A, frequencies to be measured are intermittently selected from the first frequency band FB1, and the band of the selected frequencies to be measured is set as the second frequency band FB2. That is, the width of the second frequency band FB2 is substantially equal to the width of the first frequency band FB1, but the second frequency band FB2 intermittently has frequencies to be measured as compared with the first frequency band FB1. In other words, as illustrated in FIG. 12B, the measurement unit 30 performs measurement in the second mode at wider measurement spacings (second frequency spacing) than the measurement spacings (first frequency spacing) in the first mode. Therefore, the sensor device 10 can detect the water content in a short time and with low power consumption. In addition, since the width of the second frequency band FB2 is substantially equal to the width of the first frequency band FB1, the water content can be detected relatively accurately even in the second mode.

Figure 13A:
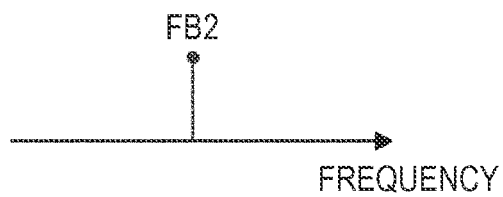
FIG. 13A is a graph illustrating still another modification example of the second frequency band.
Figure 13B:
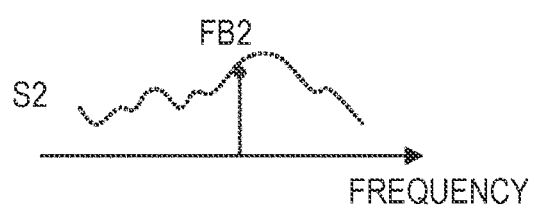
FIG. 13B is a graph illustrating the modification example of the second frequency band.
Figure 13C:
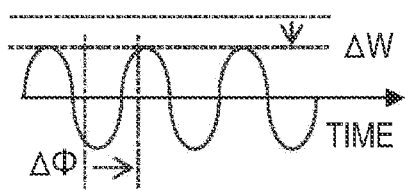
FIG. 13C is a graph illustrating the modification example of the second frequency band.

FIGS. 13A to 13C are graphs illustrating still another modification example of the second frequency band. In FIG. 13A, the second frequency band FB2 is one specific frequency in the first frequency band FB1. In this case, as illustrated in FIG. 13B, the measurement unit 30 performs measurement at a specific frequency in the second mode. Therefore, the sensor device 10 can detect the water content in a very short time and with very low power consumption.

In this case, an amplitude difference $\Delta W$ or a phase difference $\Delta \Phi$ illustrated in FIG. 13C can be used as the characteristic amount. The amplitude difference $\Delta W$ represents a difference (amplitude attenuation width) between the level of the transmission signal F in FIG. 13A and the level of the measurement signal S2 in FIG. 13B. The phase difference $\Delta \Phi$ represents a phase delay of the level of the measurement signal S2 with respect to the transmission signal F. Note that, in the first mode, the relationship information generation unit 55 can generate the relationship information using, instead of the partial delay time DL12, the amplitude difference or the phase difference of the measurement signal S1 at the specific frequency as the first characteristic amount. Therefore, the vertical axis in FIG. 6 represents the amplitude difference or the phase difference of the measurement signal S1 at the specific frequency. That is, in this modification example, the relationship information is a relational expression or correspondence table between the amplitude difference or the phase difference and the first propagation delay time DL11.

In the second mode, the signal processing unit 50 calculates the propagation delay time DL21 of the medium M by applying the amplitude difference $\Delta W$ or the phase difference $\Delta \Phi$ of the measurement signal at the specific frequency as a second characteristic amount to the relationship information. In this manner, the characteristic amount may be an amplitude difference or a phase difference of the measurement signal at a specific frequency.

Note that the higher the specific frequency, the larger the phase difference $\Delta \Phi$ with respect to the propagation delay time. Therefore, in order to improve the measurement accuracy, the specific frequency is preferably a high frequency. On the other hand, since the phase difference $\Delta \Phi$ may rotate by 360 degrees or more, the specific frequency may not be measured if the specific frequency is high. Therefore, it is preferable to use a plurality of specific frequencies in the second frequency band FB2. With this arrangement, a situation in which measurement becomes impossible due to phase rotation can be prevented. Alternatively, both the amplitude difference and the phase difference of the measurement signal at the specific frequency may be used as the characteristic amounts.

Modification Example of Characteristic Amount

As described with reference to FIGS. 13A to 13C, the characteristic amount is not limited to the propagation delay time, and may be the amplitude difference or the phase difference. Further, the characteristic amount may be the shape of the frequency characteristic or the time waveform of the propagation delay time of the measurement signal S2.
(Shape of Frequency Characteristic)

Figure 14A:
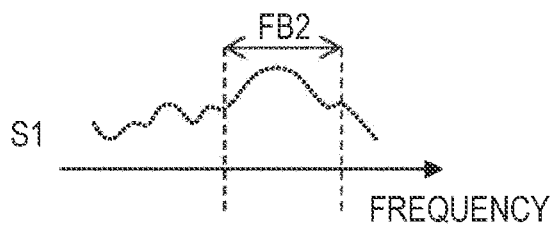
FIG. 14A is a diagram illustrating the shape of the frequency characteristic of the measurement signal.
Figure 14B:
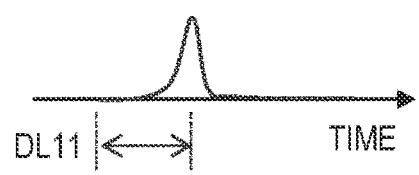
FIG. 14B is a diagram illustrating the first propagation delay time obtained from the measurement signal.

For example, FIG. 14A is a diagram illustrating the frequency characteristic of the measurement signal S1. FIG. 14B is a diagram illustrating the first propagation delay time DL11 obtained from the measurement signal S1. The signal processing unit 50 extracts the characteristic of the second frequency band FB2 from the frequency characteristic in FIG. 14A, and stores the characteristic in the memory 54 in association with the first propagation delay time DL11. In the first mode, every time steps 102 to 105 are repeated, the relationship information between the characteristic of the second frequency band FB2 and the first propagation delay time DL11 is stored. As a result, a plurality of pieces of relationship information is stored in the memory 54.

In the second mode, upon obtaining the measurement signal S2 in the second frequency band FB2, the signal processing unit 50 searches relationship information having a characteristic close to the waveform of the measurement signal S2. Then, the signal processing unit 50 obtains the first propagation delay time DL11 from the relationship information hit in the search. The signal processing unit 50 is only required to calculate the relative permittivity and the water content of the medium M using the first propagation delay time DL11 obtained from the relationship information as the corrected delay time DL21. In the present modification example, in the second mode, the signal processing unit 50 does not need to calculate the second propagation delay time DL22. Therefore, the load on the signal processing unit 50 can be reduced.
(Time Waveform of Propagation Delay Time)

Figure 15A:
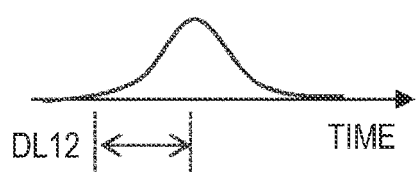
FIG. 15A is a diagram illustrating the time waveform of the partial delay time.
Figure 15B:
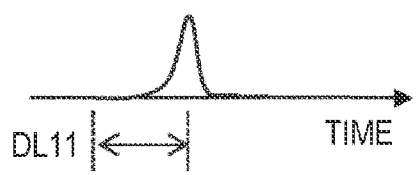
FIG. 15B is a diagram illustrating the time waveform of the first propagation delay time.

For example, FIG. 15A is a diagram illustrating the time waveform of the partial delay time DL12 similarly to FIG. 5E. FIG. 15B is a diagram illustrating the time waveform of the first propagation delay time DL11 similarly to FIG. 5C. In this modification example, the signal processing unit 50 stores the time waveform of the partial delay time DL12 in FIG. 15A in the memory 54 in association with the first propagation delay time DL11. In the first mode, every time steps 102 to 105 are repeated, the relationship information between the waveform of the partial delay time DL12 and the first propagation delay time DL11 is stored. As a result, a plurality of pieces of relationship information is stored in the memory 54.

In the second mode, the signal processing unit 50 obtains the time waveform of the partial delay time DL22 from the measurement signal S2 in the second frequency band FB2, and searches relationship information having a waveform close to the time waveform of the partial delay time DL22. Then, the signal processing unit 50 obtains the first propagation delay time DL11 from the relationship information hit in the search. The signal processing unit 50 is only required to calculate the relative permittivity and the water content of the medium M using the first propagation delay time DL11 obtained from the relationship information as the corrected delay time DL21.

In this manner, the sensor device 10 may use the shape of the frequency characteristic or the time waveform of the propagation delay time of the measurement signal S2 as the characteristic amount.

(About Multipath)

Figure 16A:
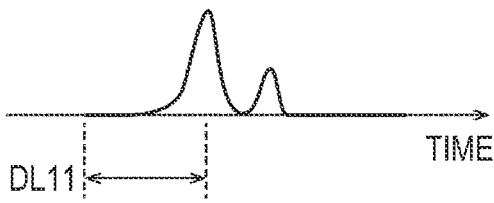
FIG. 16A is a graph illustrating an example of the first propagation delay time in the first mode.
Figure 16B:
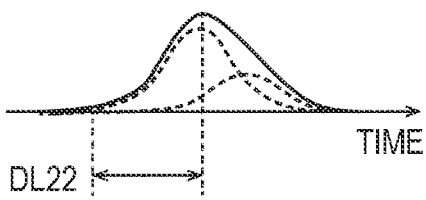
FIG. 16B is a graph illustrating an example of the second propagation delay time in the second mode.

FIG. 16A is a graph illustrating an example of the first propagation delay time DL11 in the first mode. FIG. 16B is a graph illustrating an example of the second propagation delay time DL22 in the second mode. In a case where the electromagnetic wave EW propagates through a plurality of paths (multipath) in the medium M, the resolution of the first mode is relatively high, and thus, as illustrated in FIG. 16A, a plurality of peaks appears in the first propagation delay time DL11. In this case, the multiple paths can clearly be distinguished, and the waveforms of the respective paths can easily be separated.

On the other hand, since the resolution of the second mode is relatively low, a plurality of peaks overlaps in the second propagation delay time DL22 as illustrated in FIG. 16B, and the multiple paths cannot clearly be distinguished. In this case, the second propagation delay time DL22 deviates to some extent from the propagation delay time in the main path.

In such a case, in the first mode, the signal processing unit 50 calculates the first propagation delay time DL11 of the main path out of the multiple paths. At the same time, the signal processing unit 50 extracts the measurement signal part in the second frequency band from the measurement signal S1 in a state of including the influence of the multipath, and calculates the partial delay time DL12. The relationship information is derived by performing step 106. As a result, the relationship information represents the relationship between the first propagation delay time DL11 including the influence of only the main path and the partial delay time DL12 including the influence of the multipath.

Therefore, in the second mode, even in a case where the second propagation delay time DL22 includes the influence of the multipath, the signal processing unit 50 can calculate the corrected delay time DL21 considering only the main path by using the relationship information. In this manner, the sensor device 10 according to the present embodiment can separately obtain the corrected delay time DL21 of the main path while excluding the influence of the multipath.

(About Probe)

Figure 17:
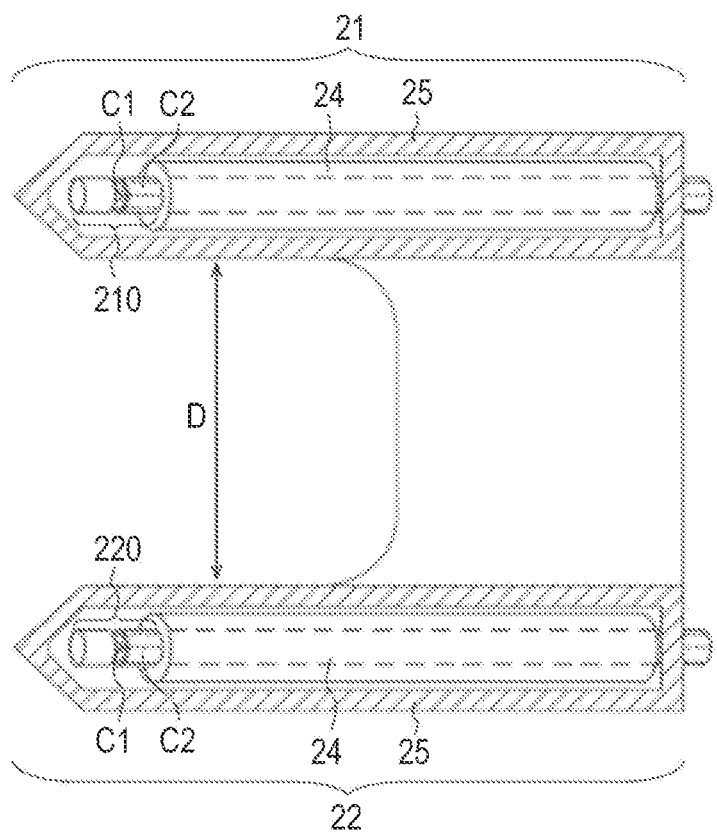
FIG. 17 is a schematic view illustrating a modification example of probes.
Figure 18:
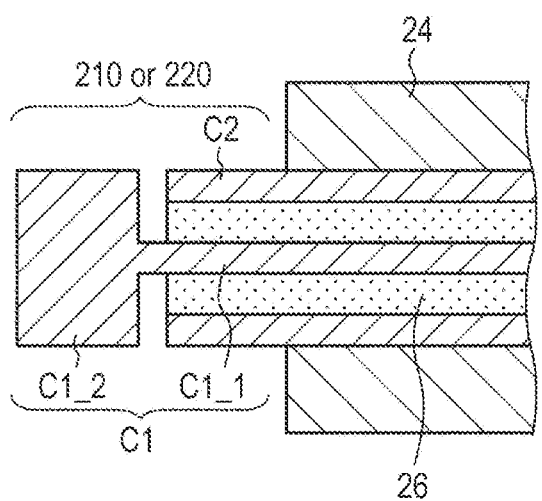
FIG. 18 is a schematic view illustrating a configuration example of the tip end portion of the probe according to the present modification example.

FIG. 17 is a schematic view illustrating a modification example of the probes 21 and 22. FIG. 18 is a schematic view illustrating a configuration example of the tip end portion of the probe 21 or 22 according to the present modification example.

Each of the transmission probe 21 and the reception probe 22 is a coaxial cable including a core wire portion C1 and a shield portion C2. The core wire portion C1 includes a copper wire, and the shield portion C2 includes a copper pipe. However, the shield portion C2 may include a mesh body of a copper wire. The outer surface of the shield portion C2 is covered with a protective layer (not illustrated) including an insulating material, and includes the sleeve 24 containing an electromagnetic wave absorbing material on the outer side thereof. Further, a cover 25 having a sharp tip end is provided outside the sleeve 24. The cover 25 is provided to allow the transmission probe 21 and the reception probe 22 to be easily inserted into the medium M and to protect the core wire portion C1 and the shield portion C2. The tip end portions of the core wire portion C1 and the shield portion C2 are exposed from the sleeve 24, and constitute the antenna units 210 and 220.

As illustrated in FIG. 18, the core wire portion C1 includes an inner portion $C1\_1$ provided inside the shield portion C2, a tip end portion $C1\_2$ protruding from the tip end of the shield portion C2, and an insulator 26 provided between the inner portion $C1\_1$ and the shield portion C2. For the inner portion $C1\_1$ and the tip end portion $C1\_2$, a conductor such as copper is used, for example. For the insulator 26, Teflon, polyethylene, or the like having a predetermined relative permittivity is used, for example.

The inner portion $C1\_1$ has a shorter outside diameter than the inside diameter of the shield portion C2, and is separated from and insulated from the shield portion C2. Also, the tip end portion $C1\_2$ is longer than the inside diameter of the shield portion C2, but protrudes to the outside of the shield portion C2, and is provided so as to be separated from the shield portion C2. Therefore, the core wire portion C1 is electrically insulated from the shield portion C2.

By using the probes 21 and 22 having such configurations, the radiation efficiency can be increased.

Embodiments of the present technology are not limited to the above embodiments, and various changes can be made without departing from the scope of the present technology.

(1)

A detection device including:

a first probe that includes a first antenna unit for transmission;

a second probe that includes a second antenna unit for reception, the second probe being opposed to the first probe at a predetermined distance;

a measurement unit that measures a measurement signal including information regarding a propagation characteristic of an electromagnetic wave in a medium between the first and second antenna units; and a calculation unit that calculates characteristics information of the medium on the basis of a characteristic amount obtained from the measurement signal, in which, in a first mode, the measurement unit measures the measurement signal in a first frequency band for the electromagnetic wave propagating in the medium, and the calculation unit calculates the characteristics information of the medium on the basis of a first characteristic amount obtained from the measurement signal in the first frequency band, and in a second mode, the measurement unit measures the measurement signal in a second frequency band, which is a part of the first frequency band for the electromagnetic wave, and the calculation unit calculates the characteristics information of the medium on the basis of a second characteristic amount obtained from the measurement signal in the second frequency band.

(2)

The detection device according to (1), in which, in the first mode, the calculation unit generates relationship information between the first characteristic amount and a partial characteristic amount on the basis of the partial characteristic amount obtained from the measurement signal in the second frequency band out of the measurement signal in the first frequency band, and in the second mode, the calculation unit calculates the characteristics information of the medium by applying the second characteristic amount to the relationship information.

(3)

The detection device according to (1) or (2), in which the second frequency band is a band including a peak frequency at which an intensity of the measurement signal in the first frequency band is maximum.

(4)

The detection device according to (1) or (2), in which, in the first mode, the measurement unit measures the electromagnetic wave at a first frequency spacing, and in the second mode, the measurement unit measures the electromagnetic wave at a second frequency spacing wider than the first frequency spacing.

(5)

The detection device according to claim 4, in which a width of the second frequency band is substantially equal to a width of the first frequency band.

(6)

The detection device according to (1) or (2), in which the second frequency band is a specific frequency in the first frequency band.

(7)

The detection device according to any one of (1) to (5), in which the characteristic amount is a propagation delay time of the electromagnetic wave between the first and second antenna units, a shape of a frequency characteristic of the electromagnetic wave, or a waveform of the propagation delay time obtained on the basis of the frequency characteristic of the electromagnetic wave.

(8)

The detection device according to (6), in which the characteristic amount is a phase or an amplitude of the electromagnetic wave at the specific frequency.

(9)

The detection device according to any one of (2) to (8), in which the calculation unit includes:

a delay time calculation unit that calculates a propagation delay time of the electromagnetic wave between the first and second probes as the characteristic amount on the basis of the measurement signal;

a relative permittivity calculation unit that calculates a relative permittivity of the medium as the characteristics information on the basis of the propagation delay time;

a water content calculation unit that calculates a water content in the medium on the basis of the relative permittivity; and a relationship information generation unit (55) that generates the relationship information.

(10)

The detection device according to (9), in which, in the first mode, the calculation unit calculates a first propagation delay time on the basis of the measurement signal in the first frequency band, calculates a partial delay time obtained from the measurement signal in the second frequency band out of the measurement signal in the first frequency band, and generates the relationship information using the first propagation delay time and the partial delay time, and in the second mode, the calculation unit calculates a second propagation delay time on the basis of the measurement signal in the second frequency band, generates a corrected delay time obtained by converting the second propagation delay time into a propagation delay time in the first frequency band by applying the second propagation delay time to the relationship information, and calculates a relative permittivity of the medium and a water content in the medium using the corrected delay time.

(11)

The detection device according to any one of (1) to (10), further including a mode switching unit that switches between the first mode and the second mode.

(12)

The detection device according to any one of (1) to (11), in which, in the second frequency band, an upper limit of a level of the transmission signal out of the first frequency band is higher than an upper limit of a level in another frequency band, and in the second frequency band, the first antenna unit sets the level of the transmission signal to be higher than that in the another frequency band in the first frequency band.

(13)

A detection method using a detection device including a first probe that includes a first antenna unit for transmission, a second probe that includes a second antenna unit for reception, the second probe being opposed to the first probe at a predetermined distance, a measurement unit that measures a measurement signal including information regarding a propagation characteristic of an electromagnetic wave in a medium between the first and second antenna units, and a calculation unit that calculates characteristics information of the medium on the basis of a characteristic amount obtained from the measurement signal, the detection method including:

in a first mode, measuring the measurement signal in a first frequency band for the electromagnetic wave propagating in the medium, and calculating the characteristics information of the medium on the basis of a first characteristic amount obtained from the measurement signal in the first frequency band; and in a second mode, measuring the measurement signal in a second frequency band, which is a part of the first frequency band for the electromagnetic wave, and calculating the characteristics information of the medium on the basis of a second characteristic amount obtained from the measurement signal in the second frequency band.

(14)

The detection method according to (13), in which, in the first mode, the calculation unit generates relationship information between the first characteristic amount and a partial characteristic amount on the basis of the partial characteristic amount obtained from the measurement signal in the second frequency band out of the measurement signal in the first frequency band, and in the second mode, the calculation unit calculates the characteristics information of the medium by applying the second characteristic amount to the relationship information.

(15)

The detection method according to (13) or (14), in which the second frequency band is a band including a peak frequency at which an intensity of the measurement signal in the first frequency band is maximum.

(16)

The detection method according to any one of (13) to (15), in which, in the first mode, the measurement unit measures the electromagnetic wave at a first frequency spacing, and in the second mode, the measurement unit measures the electromagnetic wave at a second frequency spacing wider than the first frequency spacing.

(17)

The detection method according to (16), in which a width of the second frequency band is substantially equal to a width of the first frequency band.

(18)

The detection method according to (13) or (14), in which the second frequency band is a specific frequency in the first frequency band.

(19)

The detection method according to any one of (13) to (17), in which the characteristic amount is a propagation delay time of the electromagnetic wave between the first and second antenna units, a shape of a frequency characteristic of the electromagnetic wave, or a waveform of the propagation delay time obtained on the basis of the frequency characteristic of the electromagnetic wave.

(20)

The detection method according to (18), in which the characteristic amount is a phase or an amplitude of the electromagnetic wave at the specific frequency.

(21)

The detection method according to any one of (14) to (20), in which, in the first mode, the calculation unit calculates a first propagation delay time on the basis of the measurement signal in the first frequency band, calculates a partial delay time obtained from the measurement signal in the second frequency band out of the measurement signal in the first frequency band, and generates the relationship information using the first propagation delay time and the partial delay time, and in the second mode, the calculation unit calculates a second propagation delay time on the basis of the measurement signal in the second frequency band, generates a corrected delay time obtained by converting the second propagation delay time into a propagation delay time in the first frequency band by applying the second propagation delay time to the relationship information, and calculates a relative permittivity of the medium and a water content in the medium using the corrected delay time.

(22)

The detection method according to any one of (13) to (21), in which, in the second frequency band, an upper limit of a level of the transmission signal out of the first frequency band is higher than an upper limit of a level in another frequency band, and in the second frequency band, the first antenna unit sets the level of the transmission signal to be higher than that in the another frequency band in the first frequency band.

Note that the present disclosure is not limited to the above embodiments, and that various changes can be made without departing from the scope of the present disclosure. Also, effects described in the present description are illustrative only and shall not be limited, and other effects may exist.

REFERENCE SIGNS LIST

10 Sensor device
20 Sensor head
30 Measurement unit
21 Transmission probe
22 Reception probe
31 Signal generation unit
32 Communication unit
310 Control unit
311 Signal generator
313 Phase shifter
315 Mixer
50 Signal processing unit
51 Delay time calculation unit
52 Relative permittivity calculation unit
53 Water content calculation unit
54 Memory
55 Relationship information generation unit
56, 57 Mode switching unit
DL11 First propagation delay time
DL12 Partial delay time
DL22 Second propagation delay time
DL21 Corrected delay time
FB1 First frequency band
FB2 Second frequency band

What is claimed is:

1. A detection device comprising:
   a first probe that includes a first antenna unit for transmission;
   a second probe that includes a second antenna unit for reception, the second probe being opposed to the first probe at a predetermined distance;
   a measurement unit that measures a measurement signal including information regarding a propagation characteristic of an electromagnetic wave in a medium between the first and second antenna units; and
   a calculation unit that calculates characteristics information of the medium on a basis of a characteristic amount obtained from the measurement signal,
   wherein, in a first mode, the measurement unit measures the measurement signal in a first frequency band for the electromagnetic wave propagating in the medium, and the calculation unit calculates the characteristics information of the medium on a basis of a first characteristic amount obtained from the measurement signal in the first frequency band, and
   in a second mode, the measurement unit measures the measurement signal in a second frequency band, which is a part of the first frequency band for the electromagnetic wave, and the calculation unit calculates the characteristics information of the medium on a basis of a second characteristic amount obtained from the measurement signal in the second frequency band.

2. The detection device according to claim 1,
   wherein, in the first mode, the calculation unit generates relationship information between the first characteristic amount and a partial characteristic amount on a basis of the partial characteristic amount obtained from the measurement signal in the second frequency band out of the measurement signal in the first frequency band, and
   in the second mode, the calculation unit calculates the characteristics information of the medium by applying the second characteristic amount to the relationship information.

3. The detection device according to claim 2,
   wherein the calculation unit includes:
   a delay time calculation unit that calculates a propagation delay time of the electromagnetic wave between the first and second probes as the characteristic amount on a basis of the measurement signal;
   a relative permittivity calculation unit that calculates a relative permittivity of the medium as the characteristics information on a basis of the propagation delay time;
   a water content calculation unit that calculates a water content in the medium on a basis of the relative permittivity; and
   a relationship information generation unit that generates the relationship information.

4. The detection device according to claim 3,
wherein, in the first mode, the calculation unit calculates a first propagation delay time on a basis of the measurement signal in the first frequency band, calculates a partial delay time obtained from the measurement signal in the second frequency band out of the measurement signal in the first frequency band, and generates the relationship information using the first propagation delay time and the partial delay time, and in the second mode, the calculation unit calculates a second propagation delay time on a basis of the measurement signal in the second frequency band, generates a corrected delay time obtained by converting the second propagation delay time into a propagation delay time in the first frequency band by applying the second propagation delay time to the relationship information, and calculates a relative permittivity of the medium and a water content in the medium using the corrected delay time.

5. The detection device according to claim 1, wherein the second frequency band is a band including a peak frequency at which an intensity of the measurement signal in the first frequency band is maximum.

6. The detection device according to claim 1,
wherein, in the first mode, the measurement unit measures the electromagnetic wave at a first frequency spacing, and in the second mode, the measurement unit measures the electromagnetic wave at a second frequency spacing wider than the first frequency spacing.

7. The detection device according to claim 6, wherein a width of the second frequency band is substantially equal to a width of the first frequency band.

8. The detection device according to claim 1, wherein the second frequency band is a specific frequency in the first frequency band.

9. The detection device according to claim 8, wherein the characteristic amount is a phase or an amplitude of the electromagnetic wave at the specific frequency.

10. The detection device according to claim 1, wherein the characteristic amount is a propagation delay time of the electromagnetic wave between the first and second antenna units, a shape of a frequency characteristic of the electromagnetic wave, or a waveform of the propagation delay time obtained on a basis of the frequency characteristic of the electromagnetic wave.

11. The detection device according to claim 1,
further comprising a mode switching unit that switches between the first mode and the second mode.

12. The detection device according to claim 1,
wherein, in the second frequency band, an upper limit of a level of the transmission signal out of the first frequency band is higher than an upper limit of a level of the measurement signal in another frequency band, and in the second frequency band, the first antenna unit sets the level of the transmission signal to be higher than that in the another frequency band in the first frequency band.

13. A detection method using a detection device including a first probe that includes a first antenna unit for transmission, a second probe that includes a second antenna unit for reception, the second probe being opposed to the first probe at a predetermined distance, a measurement unit that measures a measurement signal including information regarding a propagation characteristic of an electromagnetic wave in a medium between the first and second antenna units, and a calculation unit that calculates characteristics information of the medium on a basis of a characteristic amount obtained from the measurement signal, the detection method comprising:

in a first mode, measuring the measurement signal in a first frequency band for the electromagnetic wave propagating in the medium, and calculating the characteristics information of the medium on a basis of a first characteristic amount obtained from the measurement signal in the first frequency band; and in a second mode, measuring the measurement signal in a second frequency band, which is a part of the first frequency band for the electromagnetic wave, and calculating the characteristics information of the medium on a basis of a second characteristic amount obtained from the measurement signal in the second frequency band.

14. The detection method according to claim 13,
wherein, in the first mode, the calculation unit generates relationship information between the first characteristic amount and a partial characteristic amount on a basis of the partial characteristic amount obtained from the measurement signal in the second frequency band out of the measurement signal in the first frequency band, and in the second mode, the calculation unit calculates the characteristics information of the medium by applying the second characteristic amount to the relationship information.

15. The detection method according to claim 14,
wherein, in the first mode, the calculation unit calculates a first propagation delay time on a basis of the measurement signal in the first frequency band, calculates a partial delay time obtained from the measurement signal in the second frequency band out of the measurement signal in the first frequency band, and generates the relationship information using the first propagation delay time and the partial delay time, and in the second mode, the calculation unit calculates a second propagation delay time on a basis of the measurement signal in the second frequency band, generates a corrected delay time obtained by converting the second propagation delay time into a propagation delay time in the first frequency band by applying the second propagation delay time to the relationship information, and calculates a relative permittivity of the medium and a water content in the medium using the corrected delay time.

16. The detection method according to claim 13,
wherein the second frequency band is a band including a peak frequency at which an intensity of the measurement signal in the first frequency band is maximum.

17. The detection method according to claim 13,
wherein, in the first mode, the measurement unit measures the electromagnetic wave at a first frequency spacing, and in the second mode, the measurement unit measures the electromagnetic wave at a second frequency spacing wider than the first frequency spacing.

18. The detection method according to claim 17,
wherein a width of the second frequency band is substantially equal to a width of the first frequency band.

19. The detection method according to claim 13,
wherein the second frequency band is a specific frequency in the first frequency band.

20. The detection method according to claim 19,
wherein the characteristic amount is a phase or an amplitude of the electromagnetic wave at the specific frequency.

21. The detection method according to claim 13,
wherein the characteristic amount is a propagation delay time of the electromagnetic wave between the first and second antenna units, a shape of a frequency characteristic of the electromagnetic wave, or a waveform of the propagation delay time obtained on a basis of the frequency characteristic of the electromagnetic wave.

22. The detection method according to claim 13,
wherein, in the second frequency band, an upper limit of a level of the transmission signal out of the first frequency band is higher than an upper limit of a level of the measurement signal in another frequency band, and in the second frequency band, the first antenna unit sets the level of the transmission signal to be higher than that in the another frequency band in the first frequency band.

* * * * *